(12) United States Patent
Jongejan et al.

(10) Patent No.: US 8,464,707 B2
(45) Date of Patent: Jun. 18, 2013

(54) COMPLIANCE MONITOR AND METHOD

(75) Inventors: Roberto Jongejan, Amsterdam (NL); Antje-Henriette Fink-Wagner, Constance (DE); Christopher Ferris, Arlesey (GB)

(73) Assignee: Takeda GmbH, Constance (DE)

( * ) Notice: Subject to any disclaimer, the term of this patent is extended or adjusted under 35 U.S.C. 154(b) by 863 days.

(21) Appl. No.: 10/572,316

(22) PCT Filed: Sep. 22, 2004

(86) PCT No.: PCT/EP2004/052265
§ 371 (c)(1),
(2), (4) Date: Mar. 17, 2006

(87) PCT Pub. No.: WO2005/028008
PCT Pub. Date: Mar. 31, 2005

(65) Prior Publication Data
US 2007/0023034 A1    Feb. 1, 2007

(30) Foreign Application Priority Data
Sep. 24, 2003  (GB) ................................. 0322361.7

(51) Int. Cl.
*A61M 11/00*    (2006.01)

(52) U.S. Cl.
USPC ............ 128/200.23; 128/200.14; 128/200.15; 128/202.22

(58) Field of Classification Search
USPC ............. 128/200.23, 200.14, 202.22, 204.23, 128/200.24, 200.15, 204.26, 207.27; 600/547
See application file for complete search history.

(56) References Cited

U.S. PATENT DOCUMENTS

| 5,261,424 | A | * | 11/1993 | Sprinkel, Jr. ................... | 131/329 |
| 5,284,133 | A | * | 2/1994 | Burns et al. ............... | 128/200.23 |
| 5,363,842 | A | | 11/1994 | Mishelevich et al. | |
| 5,544,647 | A | * | 8/1996 | Jewett et al. ............. | 128/200.23 |
| 5,692,492 | A | | 12/1997 | Bruna et al. | |
| 5,809,997 | A | * | 9/1998 | Wolf ......................... | 128/200.23 |
| 6,119,684 | A | | 9/2000 | Nöhl et al. | |
| 6,684,880 | B2 | * | 2/2004 | Trueba ..................... | 128/200.16 |
| 6,733,464 | B2 | * | 5/2004 | Olbrich et al. ................ | 600/538 |
| 6,932,083 | B2 | * | 8/2005 | Jones et al. .............. | 128/200.23 |
| 7,073,499 | B1 | * | 7/2006 | Reinhold et al. ......... | 128/200.18 |
| 2004/0187871 | A1 | * | 9/2004 | Kimmel et al. .......... | 128/204.23 |

FOREIGN PATENT DOCUMENTS

| WO | 93/12823 | A2 | 7/1993 |
| WO | 95/26212 | A1 | 10/1995 |
| WO | 97/13553 | A1 | 4/1997 |
| WO | 98/52542 | A1 | 11/1998 |

(Continued)

*Primary Examiner* — Justine Yu
*Assistant Examiner* — Colin W Stuart
(74) *Attorney, Agent, or Firm* — Nath, Goldberg & Meyer; Sheldon M. McGee; Scott Langford (57) ABSTRACT

A compliance monitor (20) is attachable to or forms part of a drug delivery device, such as an inhaler (2). The monitor comprises a flexible portion (38) to enable a switch which is actuated by a user when delivering a dose of medicament. The monitor further comprises a sensor for sensing whether the device is properly positioned in contact with or relative to the user's body for administration of the medicament. For example, where the device is an inhaler and the sensor a temperature sensor, temperature variations caused by insertion of an inhaler mouthpiece into the user's mouth indicate whether the dose has been delivered into the patient's mouth. A memory in the compliance monitor stores a compliance record indicating whether or not the device was properly positioned each time a dose was delivered.

13 Claims, 8 Drawing Sheets

FOREIGN PATENT DOCUMENTS

| | | |
|---|---|---|
| WO | 9907425 A1 | 2/1999 |
| WO | 00/69496 A1 | 11/2000 |
| WO | 01/24690 A2 | 4/2001 |
| WO | 03/020349 A2 | 3/2003 |
| WO | 03/070304 A1 | 8/2003 |

\* cited by examiner

COMPLIANCE MONITOR AND METHOD

This application was filed under 35 U.S.C. 371 as a national stage of PCT/EP2004/052265, filed Sep. 22, 2004.

The invention relates to a compliance monitor and method for a drug delivery device.

Many types of drug delivery device are used by patients, or users, without continuous supervision by a physician or medical practitioner. For example, an asthma inhaler may be provided by a physician to a user, for the user to take doses either according to a predetermined schedule or when necessitated by the user's symptoms. It is then difficult for the physician to monitor the user's use of the drug delivery device and what dosage they have taken.

One type of inhaler is a pressurised metered dose inhaler (PMDI) as described in patent application WO 98/52542, which describes the Ciclesonide MDI device and formulation.

SUMMARY OF INVENTION

The invention provides a compliance monitor and method as defined in the appended independent claims. Preferred or advantageous features of the invention are set out in dependent sub-claims.

The invention may thus advantageously provide a compliance monitor which is attachable to, or forms part of, a drug delivery device, and which stores a compliance record indicating for each delivery of a dose of a drug or medicament from the device whether the device was properly positioned for administration of the drug. Proper positioning may vary depending on the device and the drug; for example for an orally or nasally administered drug, proper positioning is positioning of the device in or near the user's mouth or nose. For delivery on or through the skin, proper positioning would be in contact with or near the skin.

In a preferred embodiment, the invention may thus advantageously provide a compliance monitor for a drug delivery device for administering a drug orally, comprising a processor coupled to a switch, a sensor and a clock. The switch is actuatable by a user on delivering a dose from the drug delivery device. Advantageously, the switch may be arranged so that operation of the drug delivery device by the user automatically actuates the switch. The sensor enables the compliance monitor to detect whether the device is positioned in the user's mouth during delivery of the dose. For example, the sensor may detect mouth temperature or conductivity, or may detect a drop in light level, as a mouthpiece of the drug delivery device is inserted into the mouth.

When the switch is actuated, the processor records the time, as output by the clock, and records whether or not an output from the sensor indicates that the device was properly positioned in the user's mouth during delivery of the dose. If delivery of a dose is indicated by actuation of the switch but the sensor output suggests that the mouthpiece of the device was not in the user's mouth, it may be assumed that the dose was not properly delivered, as may happen, for example, if the device is accidentally actuated.

Preferably, data (the compliance record) from the compliance monitor may be downloaded to a docking station or a computer for analysis, for example by a prescribing physician or medical practitioner.

In a further aspect, the invention may provide a method for monitoring use of a drug delivery device by using a compliance monitor, comprising the steps of determining (1) whether or not the device is properly positioned in contact with or relative to the user's body for administration of a drug or medicament whenever the device is operated to deliver a dose of the drug, and (2) storing in a compliance record an indication of whether or not the device was properly positioned in the user's mouth at each operation of the device.

The drug delivery device may advantageously be for oral drug administration, and is preferably an inhaler, for example for delivering a medicine or drug such as for the treatment of asthma. Such an inhaler may comprise or house a pressurised canister containing the drug and a propellant, so that depression of the canister within the drug delivery device delivers a dose of the drug. In a preferred embodiment of the invention, the switch is arranged so that it is easily, or automatically, actuated by the user on depressing the canister.

The compliance monitor may advantageously be removably attachable to the drug delivery device. It should be attachable to the drug delivery device so as not to interfere with or affect the performance of the device in delivering the drug. (This should similarly be the case if the compliance monitor forms part of the drug delivery device or is non-removably attachable to it.) A device such as an inhaler must undergo strict appraisal before it is approved for public use, and the compliance monitor should be designed so that attaching it to or integrating it with such a drug delivery device should not require reappraisal of the device. Thus, the compliance monitor should, in the case of an inhaler, advantageously attach to the exterior of the inhaler and have no components which modify or interfere with the depression of the pressurised canister or the air or gas flow path through the inhaler.

Thus, in a preferred embodiment, the invention provides a compliance monitor which attaches to the base of an inhaler casing and in which the sensor is located on an exterior surface of the inhaler mouthpiece.

In addition, the compliance monitor actuation switch should preferably not Interfere with or alter normal operation of the drug delivery device. For example, when attached to an inhaler, the switch may be positioned at the base of the inhaler housing so that a user may operate the inhaler by applying a finger to the upper end of the canister, typically at the top of the inhaler, and a thumb to the switch at the base of the inhaler.

The sensor is preferably a temperature sensor. Advantageously, the processor takes a temperature reading from the sensor at regular intervals, typically of between 0.1 and 1.0 seconds, for example every 0.2 seconds. (The sampling rate may be temporarily increased when the switch is actuated.) In order to conserve battery life the ambient temperature can be read at longer intervals, for example every 10 or 12 minutes and the sampling rate is increased temporarily only when the switch is actuated to intervals typically of between 0.1 and 1.0 seconds, for example every 0.2 seconds, The processor may thus detect insertion of the inhaler into the user's mouth by sensing a rapid change in temperature towards the mouth temperature. Optionally, the processor may subsequently confirm that the drug delivery device was placed in the user's mouth by monitoring a change in temperature away from the mouth temperature when the device is removed from the mouth after delivery of a dose.

A rate of change of temperature towards and/or away from the mouth temperature may also be used to detect insertion of the drug delivery device into the mouth. The processor may also monitor ambient temperature, as measured by the temperature sensor before and after insertion into the mouth, and take account of the ambient temperature when determining whether or not the device was properly placed in the mouth when the dose was delivered.

The sensor may alternatively be a light sensor. The processor would then detect insertion of the drug delivery device into the mouth by looking for a characteristic change in light level. The processor would monitor ambient light levels in this case, rather than ambient temperature.

The sensor may alternatively be a conductivity sensor, for sensing a characteristic mouth conductivity when the drug delivery device is inserted into the mouth. The processor would monitor ambient conductivity in this case, rather than ambient temperature.

Alternatively, a combination of such sensors may be used.

Whichever type of sensor is used, it should advantageously be positioned externally to the drug delivery device mouthpiece so as not to interfere with operation of the device.

According to a further aspect of the invention, after a period of time such as a few days or weeks, or up to a few months or more, the compliance monitor may be coupled to a docking station or a computer to download the compliance record, for example for review by a physician or medical practitioner. The record comprises for each delivery of a dose an indication of whether the drug delivery device mouthpiece was properly placed in the user's mouth. It may also include the times at which doses have been delivered. The physician may thus determine when doses have been properly taken and when doses have been delivered incorrectly, for example into free air, whether by accidental or malicious operation of the device.

The physician may thus assess the dosage actually taken by the user. Where regular doses of drug are to be taken according to a prescription, the physician may thus assess whether the user has followed the prescription. Where doses of a drug are taken in response to symptoms, the physician may assess what dosage or dosage frequency the user has required. Often, the physician may not know if a user's continuing illness is due to not taking a drug in the prescribed manner or because the drug is not effective. The compliance monitor may report when the drug is properly used so that the physician may discover whether the user is using the drug as prescribed.

In a preferred embodiment, the compliance monitor comprises a low-power microprocessor with timing capability and memory storage to record multiple uses of the drug delivery device. The sensor is a separate component which provides an analogue input to the microprocessor, sensitive to mouth temperature or conductance, or light level, as described above. The monitor is advantageously effectively permanently switched on, so that the user does not have to intervene with monitor operation. The monitor advantageously comprises the microprocessor and other components housed in a small enclosure, which is affixed to the drug delivery device, for example by means of a clip, an adhesive, or an adhesive label. Advantageously, the monitor is relatively unobtrusive when fastened to the device.

DESCRIPTION OF SPECIFIC EMBODIMENTS AND BEST MODE OF THE INVENTION

Specific embodiments of the invention will now be described by way of example, with reference to the attached drawings in which.

Figure 1:
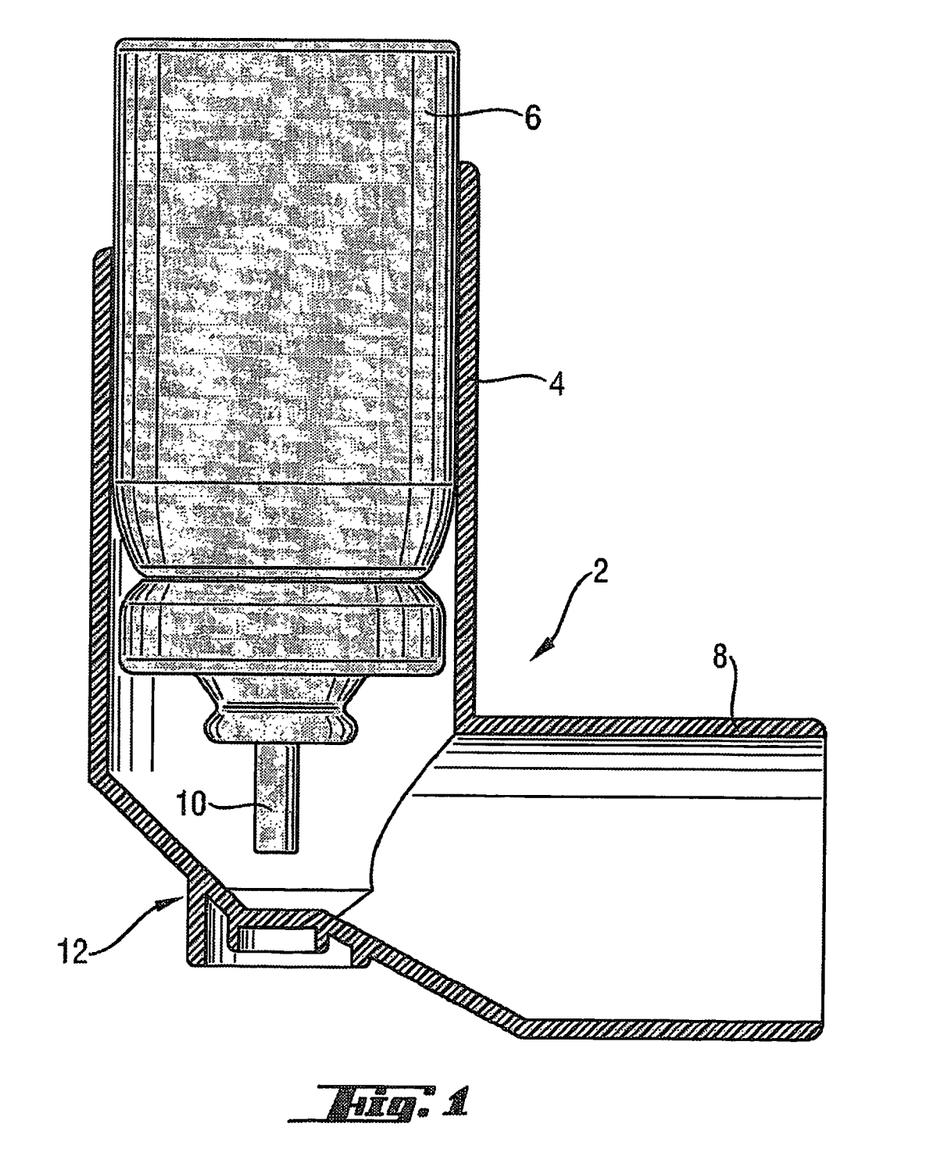
FIG. 1 is a longitudinal section of a standard pressurised metered dose inhaler (PMDI)

FIG. 1 is a longitudinal section of a conventional pressurised metered dose inhaler 2 (PMDI), in which a moulded plastics housing comprises a cylindrical portion 4 for receiving a pressurised canister 6, and a mouthpiece 8. The pressurised canister contains a drug and a propellant gas. When the canister is depressed into the housing by a user, the drug is expelled from a nozzle 10. At the same time, the mouthpiece is inserted into the user's mouth, and the user inhales to take a dose of the drug in known manner.

Figure 2:
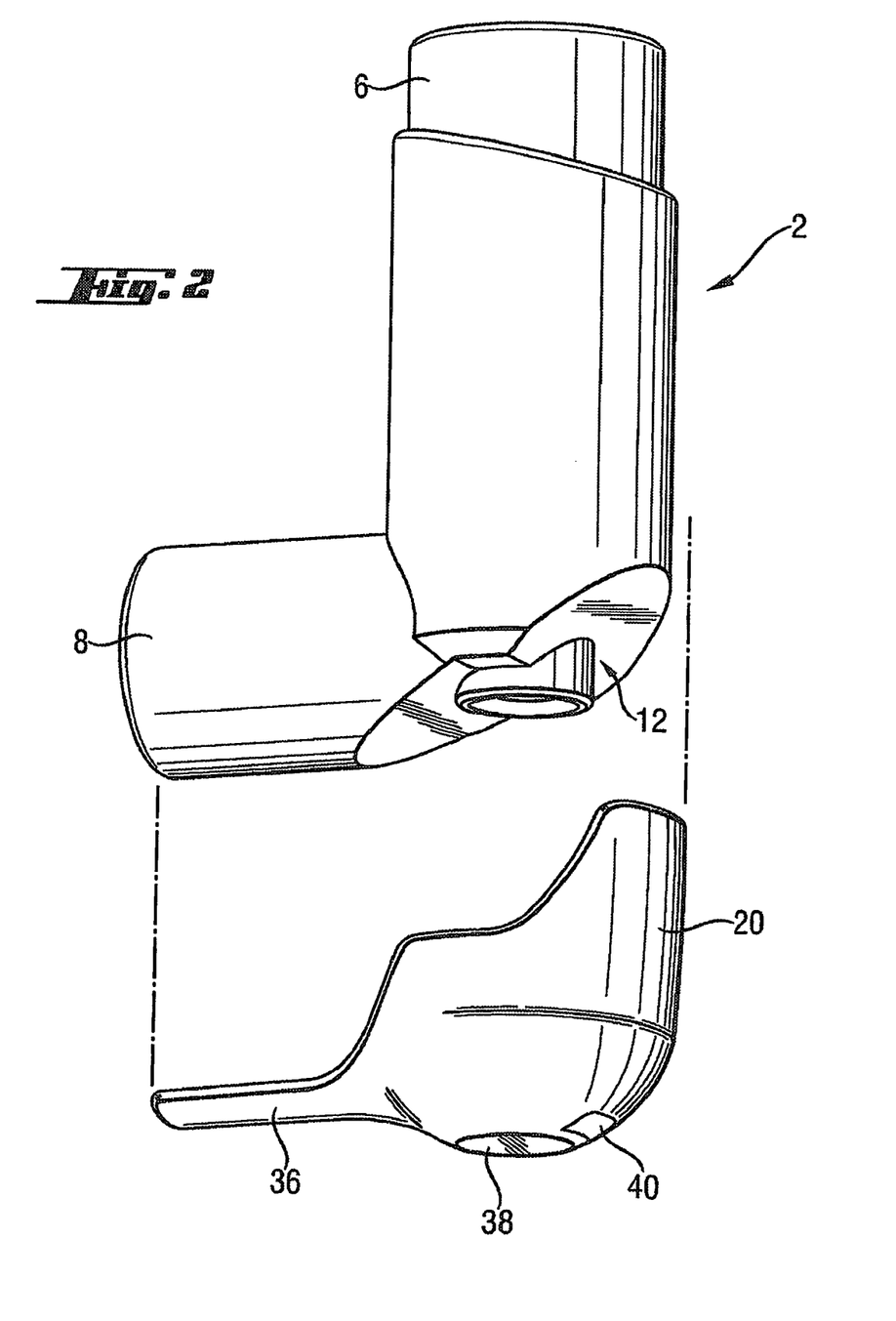
FIG. 2 is a perspective view of the PMDI of FIG. 1.

FIG. 2 is a perspective view of the PMDI, showing a generally bevelled, or cut-away, portion 12 of its exterior surface opposite the mouthpiece, at the base of the cylindrical portion opposite the exposed end of the canister which is depressed by the user.

Figure 3:
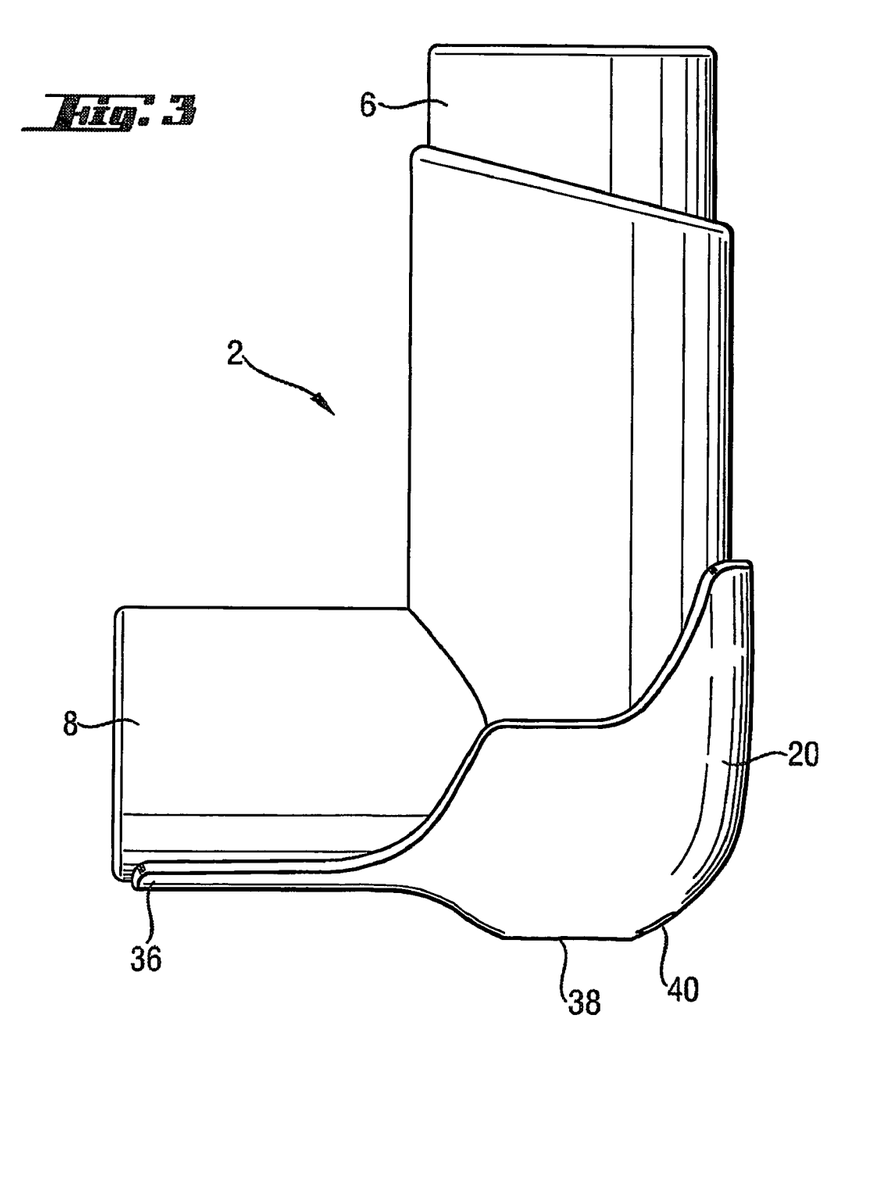
FIG. 3 is a side view of the PMDI of FIG. 1 having a compliance monitor according to a first embodiment of the invention fastened thereto.
Figure 4:
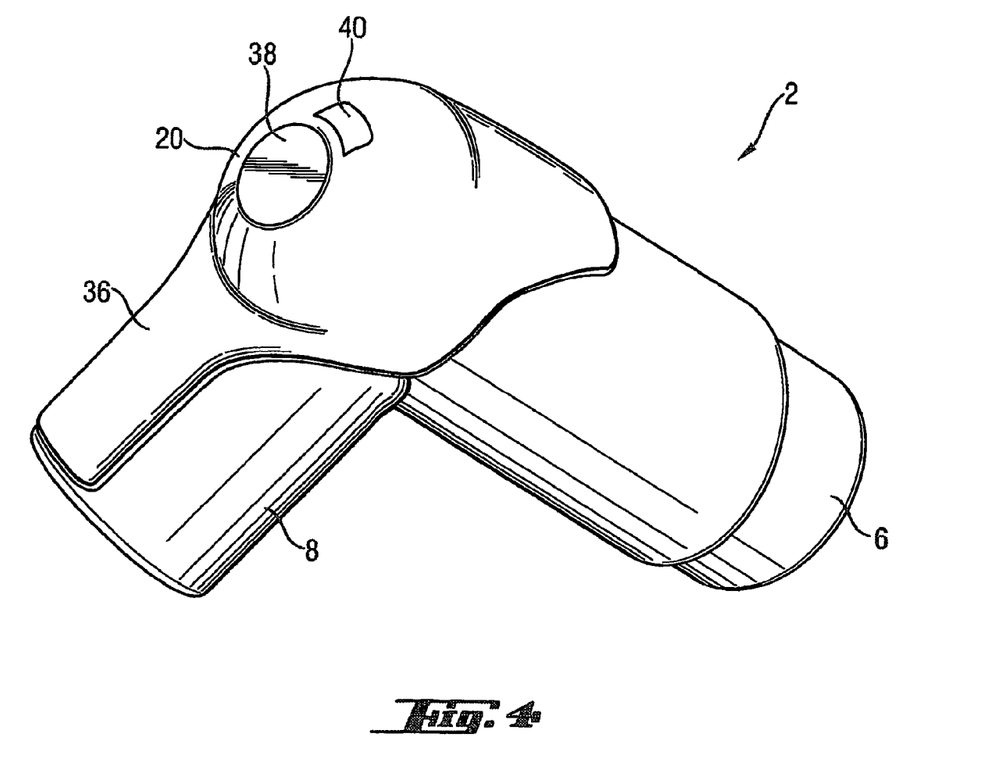
FIG. 4 is a perspective view from beneath the compliance monitor and PMDI of FIG. 3.
Figure 5:
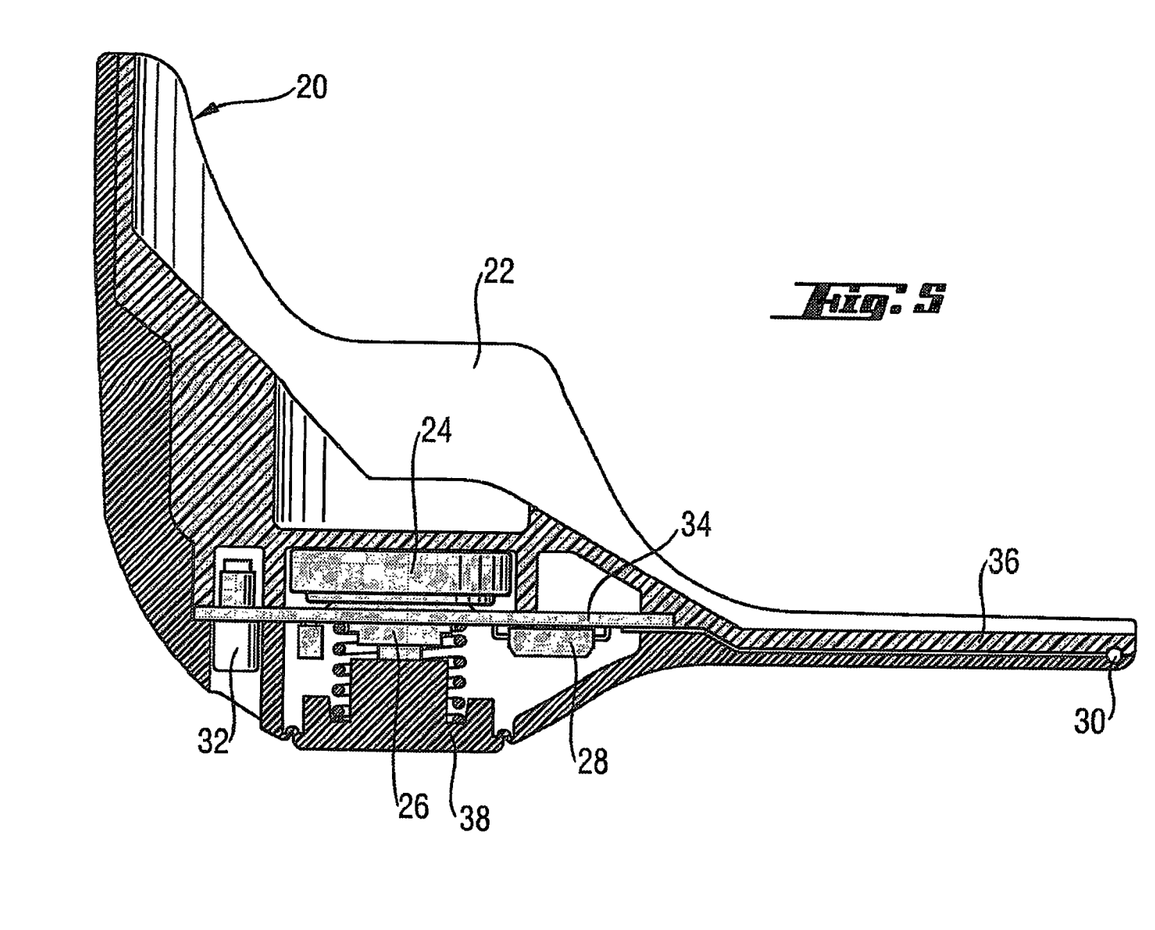
FIG. 5 is a cross section of the compliance monitor of FIG. 3.

FIGS. 3, 4 and 5 illustrate a compliance monitor 20 embodying the invention. This comprises a moulded rubber housing comprising an interface surface 22 shaped to abut the bevelled, or cut-away, portion 12 of the PMDI exterior. Advantageously, the interface surface clips onto the PMDI, but alternatively an adhesive or an adhesive label may be used to securely fasten the compliance monitor to the PMDI.

FIGS. 3 and 4 illustrate the compliance monitor in position on the PMDI. FIG. 5 shows the monitor in cross section.

Within the rubber housing are mounted a battery 24, a switch 26, an electronics module 28, a temperature sensor 30, and a set of contacts 32. The battery, electronics module, switch and contacts are mounted on a printed circuit board 34 and the temperature sensor is mounted at the end of a protruding portion 36 of the rubber housing which extends, in use, along an underside of the PMDI mouthpiece so that the temperature sensor enters or contacts the user's mouth when the mouthpiece is placed in the mouth. The rubber housing adjacent to the temperature sensor is sufficiently thin to allow rapid heat conduction from the mouth to the sensor.

The switch 26 is covered by a flexible portion 38 of the rubber housing, to enable the switch to be depressed. The contacts 32 are covered by an openable portion 40 of the rubber housing which can be removed or opened when the compliance monitor is placed in a docking station as described below.

Figure 6:
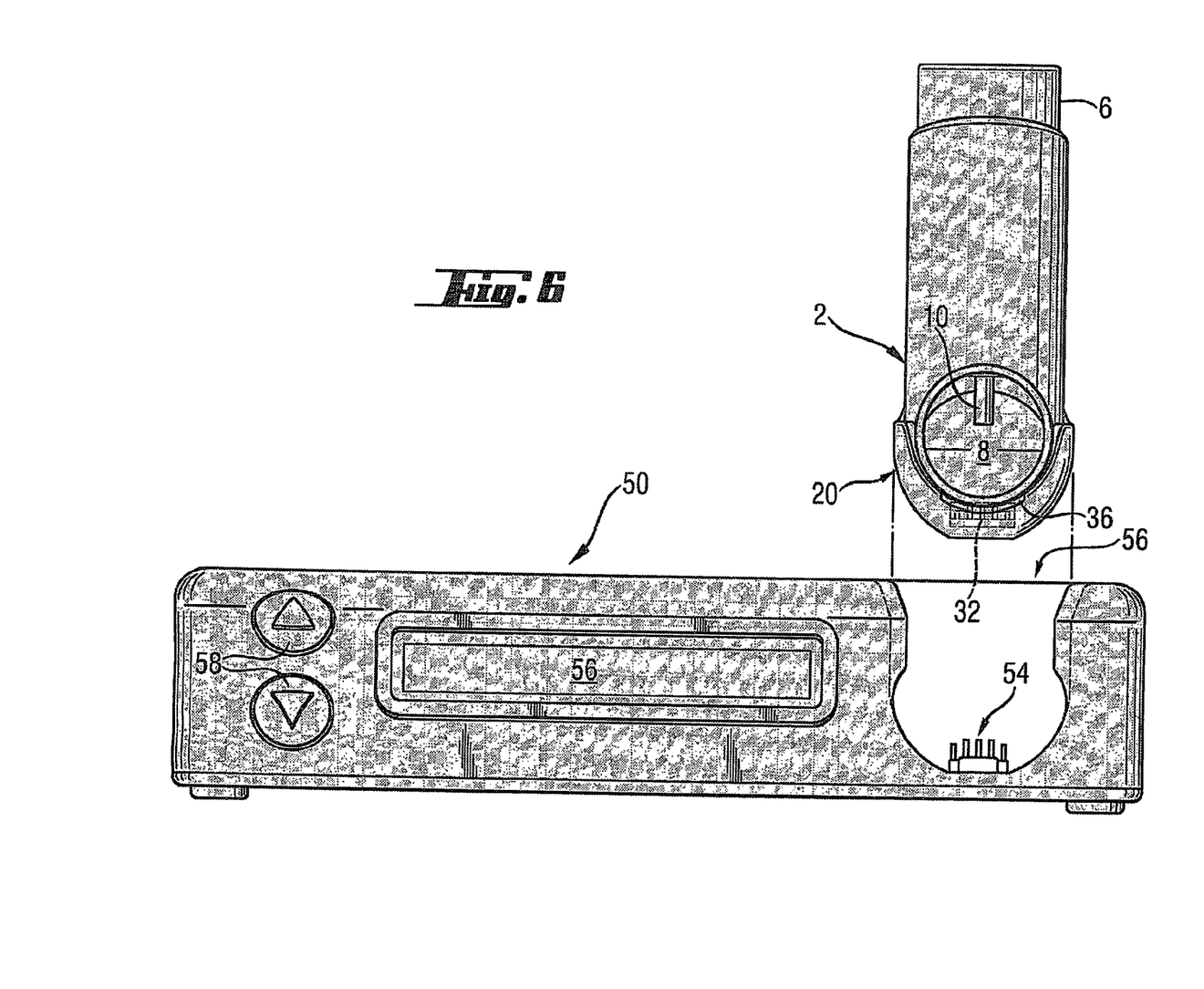
FIG. 6 is a front view of a docking station according to a further embodiment of the invention for receiving the compliance monitor and inhaler of FIG. 3.

FIG. 6 is a front view of the docking station 50 comprising a cradle 52 for receiving the compliance monitor attached to the inhaler. A set of electrical contacts 54 connects with the contacts 32 of the compliance monitor when docked. The docking station comprises a display 56 and control buttons 58 for use to review data downloaded from the compliance monitor.

Figure 7:
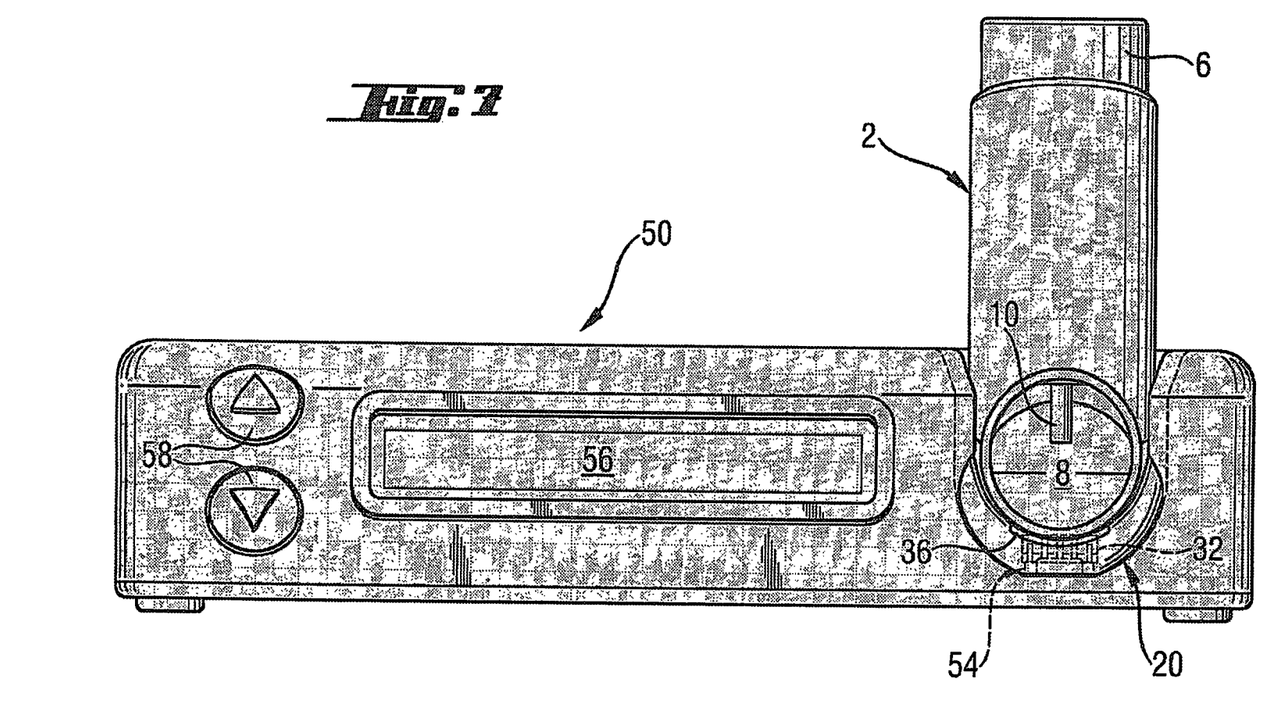
FIG. 7 is a front view of the docking station of FIG. 6 with the compliance monitor and PMDI in place.

FIG. 7 illustrates the compliance monitor and PMDI docked in the docking station 50.

Figure 8:
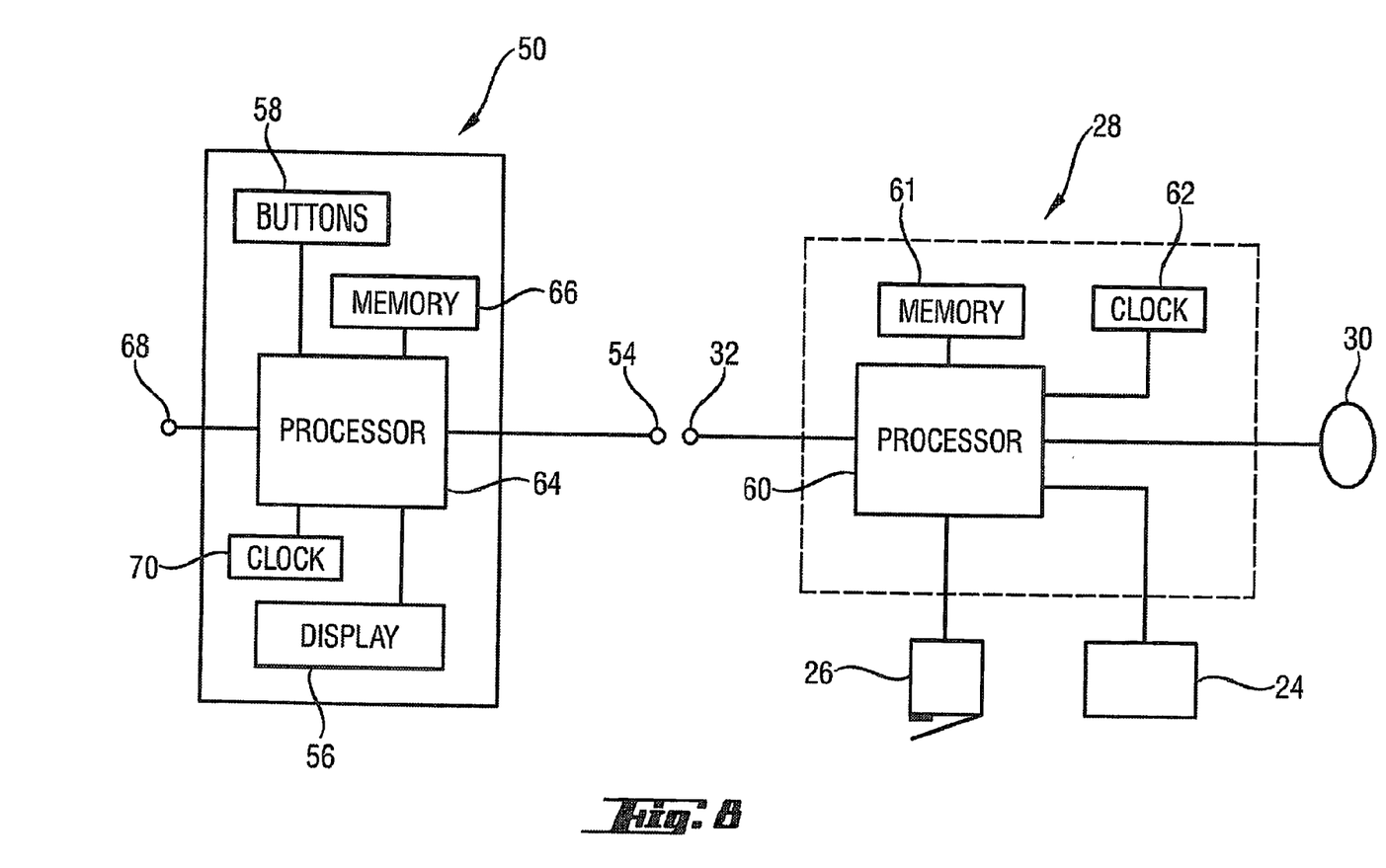
FIG. 8 is a block diagram of the circuitry of the compliance monitor and docking station.

FIG. 8 is a block diagram of the electronic circuitry of the compliance monitor and the docking station, connected by their respective contacts 32, 54.

The electronics module 28 of the compliance monitor comprises a processor 60 coupled to the contacts 32 and the switch 26 and, at an analogue input, to the temperature sensor 30. The battery 24 powers the electronics module.

Within the electronics module, the processor is coupled to a memory 61 and a clock 62.

The docking station 50 comprises a processor 64 coupled to the contacts 54, the display 56 a memory 66 and a clock 70.

The processor is controlled by means of the control buttons 58. The processor is also coupled to an interface 68, which is couplable to an external device such as a computer. The interface 68 may be, for example, a USB port or other standard interface.

When the compliance monitor is docked with the docking station, the docking station processor can interrogate the compliance monitor processor and download stored data into its own memory 66. The data can then be processed and displayed on the display screen 56 under the control of a medical practitioner through use of the buttons 58. Data downloaded from the compliance monitor is timed, using the compliance monitor clock, but this clock may not be synchronised with real time. Therefore, the clock 70 in the docking station, which is synchronised with real time, enables the data to be timed and date stamped after downloading.

An object purpose of the compliance monitor of the embodiment is to allow a physician or other medical practitioner to monitor usage of a drug delivery device such as an inhaler, or PMDI, used to treat conditions such as asthma where the regular and accurate taking of medication is necessary to treat the condition. To this end, the physician clips the compliance monitor 20 on to the PMDI body 2 and activates the monitor by connecting the battery. The combined monitor and PMDI are then supplied to the user, or patient, in the normal way.

When the user requires medication, he inserts the mouthpiece 8 into his mouth, inhales and simultaneously depresses the upper end of the pressurised canister 6 in known manner. This causes a unit dose of medication to be released and drawn by the user's breath through the mouthpiece. The compliance monitor switch is positioned on the base of the monitor such that the user can hold the monitor between finger and thumb and, while depressing the upper end of the canister, simultaneously press on the switch. The switch is positioned so that this happens automatically if the user grips the inhaler between finger (on top of the canister) and thumb (at the base of PMDI housing) in the normal way. Closure of the switch tells the processor 60 that the PMDI has been operated.

The processor 60 regularly monitors the ambient temperature close to the PMDI mouthpiece by means of the sensor 30. For example, the temperature may be monitored at intervals of between 0.1 seconds and 0.5 seconds, or 1.0 seconds.) In order to conserve battery life the ambient temperature can be read at longer intervals, for example every 10 or 12 minutes and the sampling rate is increased temporarily only when the switch is actuated to intervals typically of between 0.1 and 1.0 seconds, for example every 0.2 seconds, When the mouthpiece is inserted into the user's mouth, and the user actuates the switch, the temperature sampling rate is increased by the switch and the sensor will detect a rapid temperature change and this is signaled to the processor. Thus, a coincidence between sensing canister actuation (by means of the switch) and a rapid temperature change is taken to indicate that the drug has been delivered with the PMDI mouthpiece in the user's mouth and not, for example, in free space. This information is stored in the compliance monitor memory 61 along with a time from the clock 62. In a preferred embodiment of the invention the algorithm for detecting contact with the users mouth combines the rate of change of temperature (how fast the sensor reacts to mouth contact) and the absolute change of temperature (how much temperature change occurs). In this embodiment the recording is based on the following parameters: time between consecutive ambient measurements (e.g. 12 minutes), prevailing ambient temperature, pre-actuation time for valid ambient reading (e.g. 30 seconds), backup ambient temperature if pre- or post-actuation is invalid, time delay before first measurement (e.g. 2 seconds), temperature of first measurement, number of measurement (e.g. 4 mesurements), interval between measurements (e.g. 1 second), temperature of sensor at each subsequent measurement,—threshold of rate of change—between consecutive measurements, threshold of aggregate temperature change from ambient and post-actuation time for valid ambient reading (e.g. 30 seconds).

To explain the pre- and post-actuation times: The regular ambient reading would be corrupted if the user operates the compliance monitor at the time the ambient reading is detected. To prevent this, the backup ambient reading is used if the user operates the monitor within a short time before or after the ambient reading is sensed. The pre- and post-actuation values define when the backup ambient reading should be used.

For example an accumulative change of more than 16 degrees in 5 readings (3.2 degrees average) could be used to indicate correct use. Optionally, a rate of change threshold of 1.4 degrees per second, or a temperature change of more than 4 degrees within 5 seconds could be used, to indicate correct use.

The user continues to use the PMDI for a period determined by the physician. At the end of this time, they return the device to the physician. The physician then docks the monitor in the docking station and the stored data is transferred under control of the docking station processor 64, to the docking station memory 66. This process Is initiated by pressing one of the buttons 58 on the docking station.

The docking station's real time clock 70 enables the dosage times recorded by the compliance monitor to be converted to real times after the data has been downloaded. The data can then be presented on the docking station display in a number of forms such as the time of each event and whether the event is associated with a temperature change corresponding to the device mouthpiece in the patient's mouth. Alternatively, a statistical survey of the data can be given, such as an indication of whether doses have been taken regularly.

The buttons 58 allow the data to be scrolled on the display.

Data can also be outputted to an external device such as a computer, PC or printer through the interface 68, for example for further analysis or for remote monitoring by a physician.

The invention claimed is:

1. A compliance monitor for a drug delivery device with a mouthpiece for administering a drug, comprising:
    a switch actuatable by a user on delivering a dose from a drug delivery device;
    a sensor for detecting whether the device is properly positioned in contact with or relative to the user's body for delivery of the dose; and
    a processor coupled to the switch and the sensor for recording whether or not the device was properly positioned when the switch was actuated;
    wherein the compliance monitor is removably attachable to the mouthpiece of the drug delivery device;
    wherein the sensor is a temperature sensor for sensing body temperature and the temperature sensor is mounted so that the temperature sensor enters or contacts the user's mouth when the mouthpiece is placed in the mouth, and wherein the compliance monitor comprises a housing and the sensor is mounted at the end of a protruding portion of the housing such that the sensor does not affect the normal operation of the drug delivery device.

2. The compliance monitor according to claim 1, comprising a clock coupled to the processor and in which the time of actuation of the switch is recorded.

3. The compliance monitor according to claim 1, wherein the drug delivery device is an inhaler operated by the user depressing a pressurized canister containing the drug, and wherein the switch is a pressure-operated switch actuatable as the user depresses the canister.

4. The compliance monitor according to claim 1, in which a change in an output of a sensor characteristic of correct use of the drug delivery device is used to determine whether the device was properly positioned when the dose was delivered.

5. The compliance monitor according to claim 1, further comprising an output for downloading data to a docking station or a computer.

6. The compliance monitor according to claim 1, in which data recorded comprises a compliance record of use of the drug delivery device, including a record of whether the sensor output indicates that the device was properly positioned on each occasion that a dose has been delivered.

7. A docking station for use with the compliance monitor as defined in claim 1, the docking station and the compliance monitor comprising respective contacts.

8. A combination compliance monitor for a drug delivery device and non-transitory computer-readable medium carrying a computer program for programming a general purpose computer to receive and process data downloaded from a compliance monitor, the combination comprising:
 a compliance monitor according to claim 1; and
 a non-transitory computer-readable medium carrying a computer program for programming a general purpose computer to receive and process data downloaded from the compliance monitor according to claim 1.

9. A drug delivery device comprising a compliance monitor as defined in claim 1.

10. A method of using a compliance monitor as defined in claim 1, to monitor use of a drug delivery device for administration of a drug, comprising the steps of:
 determining when a user operates the device to deliver a dose of the drug;
 sensing whether the device is properly positioned in contact with or relative to the user's body when the dose is delivered; and
 recording for each operation of the device whether or not the device was properly positioned.

11. The method according to claim 10, further comprising the step of determining and recording the time of each operation of the device.

12. The method according to claim 10, in which the drug delivery device is for oral administration of the drug and proper positioning of the device is proper positioning in the user's mouth.

13. The method according to claim 10, further comprising the step of downloading recorded data from the compliance monitor to a docking station or a computer to allow a compliance record to be reviewed.

* * * * *